(12) United States Patent
Jang et al.

(10) Patent No.: US 9,443,351 B2
(45) Date of Patent: Sep. 13, 2016

(54) APPARATUS AND METHOD FOR RECONSTRUCTING SKELETAL IMAGE

(71) Applicant: Korea Advanced Institute of Science and Technology, Daejeon (KR)

(72) Inventors: In Gwun Jang, Daejeon (KR); Jung Jin Kim, Daejeon (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 14/680,104

(22) Filed: Apr. 7, 2015

(65) Prior Publication Data

US 2016/0163101 A1 Jun. 9, 2016

(30) Foreign Application Priority Data

Dec. 4, 2014 (KR) .......................... 10-2014-0173155

(51) Int. Cl.
*G06K 9/00* (2006.01)
*G06T 17/20* (2006.01)
*G06T 7/00* (2006.01)
*G06T 11/00* (2006.01)
*A61B 6/03* (2006.01)
*A61B 6/00* (2006.01)
*A61B 5/00* (2006.01)

(52) U.S. Cl.
CPC .......... *G06T 17/205* (2013.01); *A61B 5/4509* (2013.01); *A61B 6/032* (2013.01); *A61B 6/505* (2013.01); *G06T 7/0014* (2013.01); *G06T 7/0081* (2013.01); *G06T 11/003* (2013.01); *G06T 2200/04* (2013.01); *G06T 2207/10072* (2013.01); *G06T 2207/20141* (2013.01); *G06T 2207/30008* (2013.01); *G06T 2207/30196* (2013.01); *G06T 2210/41* (2013.01); *G06T 2219/008* (2013.01); *G06T 2219/016* (2013.01)

(58) Field of Classification Search
USPC .................................................. 382/128–134
See application file for complete search history.

(56) References Cited

U.S. PATENT DOCUMENTS

| | | | |
|---|---|---|---|
| 2005/0031179 A1* | 2/2005 | Wehrli | G01N 24/08 382/131 |
| 2005/0207630 A1* | 9/2005 | Chan | A61B 6/466 382/131 |
| 2008/0259074 A1* | 10/2008 | Tian | A61B 5/0073 345/419 |

OTHER PUBLICATIONS

In Gwun Jang; "Finite Element Method for Bone Quality Assessment Using CT"; International Biomedical Engineering Conference 2014; Apr. 18, 2014; 34 pages.
In Gwun Jang et al.; "QCT Image Enhancement for Investigating Trabecular Architecture in Proximal Femur"; The Korean Society of Radiology; Oct. 8, 2014; 18 pages.
In Gwun Jang et al.; "Quantitative Computed Tomography Image Resolution Enhancement Based on Topology Optimization"; IBEC 2014; Nov. 20, 2014; p. 291, 26 pages.

* cited by examiner

*Primary Examiner* — Alex Liew
(74) *Attorney, Agent, or Firm* — Blank Rome LLP; Michael C. Greenbaum; Jonathan R. King

(57) ABSTRACT

An apparatus and method for reconstructing a skeletal image for osteoporotic diagnosis is disclosed. A skeletal image reconstruction method may include separating a region of interest (ROI) corresponding to a skeletal system from an image captured from an inspection target, and reconstructing a high-resolution skeletal image by performing a finite element method (FEM) and topology optimization on the ROI.

20 Claims, 7 Drawing Sheets

APPARATUS AND METHOD FOR RECONSTRUCTING SKELETAL IMAGE

CROSS-REFERENCE TO RELATED APPLICATION

This application claims the priority benefit of Korean Patent Application No. 10-2014-0173155, filed on Dec. 4, 2014, in the Korean Intellectual Property Office, the disclosure of which is incorporated herein by reference.

BACKGROUND

1. Field of the Invention

The present invention relates to technology for reconstructing a skeletal image to enhance a resolution of a medical image.

2. Description of the Related Art

With the advancement to an aging society, a variety of issues such as senior citizens, welfare, and medical care have arisen. Here, osteoporosis has been regarded as a social issue to be urgently solved due to an increase in prevalence and degradation in the quality of life. For example, according to statistical data about the national health care published in 2010, the prevalence of osteoporosis studied for people of 50 or more years old showed 34.8% of women and 7.8% of men, which confirms that one in three among women over 50ties is suffering from osteoporosis. Globally, about 0.2 billions of women have the same issue.

The medical definition for osteoporosis is a progressive bone disease that a bone fracture is highly likely to occur due to a decrease in bone mass and fragility in bone strength by a qualitative change. Here, the bone strength indicates a force of bone against the fracture and is determined based on the bone mass and the bone quality.

The bone mass may be expressed as a bone mineral density (BMD). Clinically, dual energy X-ray absorptiometry (DXA), quantitative computed tomography (QCT), and computed tomography (CT) are utilized to measure the BMD. In this instance, according to a DXA based diagnosis method suggested in the World Health Organization (WHO), abnormalities may be found when 30 to 50% or more of bone mass is lost. Accordingly, the early diagnosis for osteoporosis is difficult.

Recently, the bone strength has been known to be determined based on a BMD and a structural characteristic of spongy bone. Only 64% of mechanical strength of spongy bone can be predicted only using a method of measuring only a BMD. Up to 94% of mechanical strength can be predicted by considering even a skeletal structure. In particular, a network of spongy bone cannot be recovered even with medication once the network is disconnected. In the case of a loss of the same bone mass, a decrease in trabecular connectivity further affects the bone strength compared to a decrease in a trabecular thickness.

Accordingly, both the BMD and the trabecular architecture need to be considered to perform an accurate diagnosis. However, although 50 to 200 μm high resolution that is the average trabecular thickness is required to represent a bone micro-architecture of spongy bone, a medical imaging device according to the related art may not readily provide information about the bone quality such as the bone micro-architecture due to constraints in a resolution. For example, in the case of X-ray based CT, relatively low inspection charge and relatively short inspection time are used compared to magnetic resonance imaging (MRI). However, due to a low resolution of about 600 μm, it is difficult to observe bone micro-tissues. Further, an amount of radiation exposure increases as a resolution increases. In the case of micro CT, bone micro-tissues may be imaged at a resolution of 30 μm, however, may not be readily used for clinical usage due to a high radiation amount. In addition, MRI may image a difference between signals coming from tissues through resonance using photons of a body. However, according to an increase in a resolution of an image, a scanning time increases and noise is degraded, which leads to decreasing a signal to noise ratio (SNR).

Accordingly, there is a need for an imaging technology for providing a high resolution image of 300 μm or less from which a bone micro-architecture is verifiable, without increasing an amount of radiation exposure and a scanning time.

SUMMARY

Embodiments of the present invention are to reconstruct a low-resolution image by a limited amount of radiation exposure and scanning time to a high-resolution image used to verify a bone micro-architecture using a finite element method (FEM) and topology optimization.

Also, embodiments of the present invention are to more accurately perform an early diagnosis of lesion associated with a bone mineral density (BMD) such as osteoporosis by providing a high-resolution image representing the BMD and a bone micro-architecture.

According to embodiments of the present invention, there is provided a method of reconstructing a skeletal image, the method including determining a region of interest (ROI) to be processed at a high resolution with respect to a skeletal image captured from an inspection target, and reconstructing a high-resolution skeletal image by performing an FEM and topology optimization on the ROI.

According to an aspect, the reconstruction of the skeletal image may include performing meshing on the skeletal image including the ROI, converting a BMD of bone corresponding to the meshed ROI to an elastic modulus, applying the elastic modulus to each finite element constituting the ROI, applying a predetermined load condition to a finite element model to which the elastic modulus is applied, calculating a strain energy of each finite element based on the displacement of a finite element model t to which the load condition is applied, and determining a density value of each finite element based on the strain energy of each finite element.

According to another aspect, the performing of the meshing may include segmenting the skeletal image into images including a plurality of finite elements, and the BMD of bone may indicate the BMD of bone corresponding to a finite element included in the ROI to be processed at the high resolution among the plurality of finite elements.

According to still another aspect, the reconstructing of the skeletal image may include reconstructing the high-resolution skeletal image by determining a new BMD of the ROI by performing the topology optimization, and by iteratively performing an operation of converting the new BMD to an elastic modulus.

According to still another aspect, the skeletal image reconstruction method may further include calculating a BMD of each finite element included in the ROI based on an objective function indicating a strain energy of the ROI and a predetermined constraint, and estimating presence or absence of lesion of the inspection target based on the calculated BMD and the skeletal image.

According to still another aspect, the high-resolution skeletal image may include a trabecular bone architecture corresponding to the ROI.

According to still another aspect, the high-resolution skeletal image may indicate an image having a resolution of 300 μm or less.

According to embodiments of the present invention, there is provided an apparatus for reconstructing a skeletal image, the apparatus including an ROI determiner configured to determine an ROI to be processed at a high resolution with respect to a skeletal image captured from an inspection target, and an image reconfigurer configured to reconstruct a high-resolution skeletal image by performing an FEM and topology optimization on the ROI.

According to an aspect, the image reconfigurer may be configured to perform meshing on the skeletal image including the ROI, to convert a BMD of bone corresponding to the meshed ROI to an elastic modulus, to apply the elastic modulus to each finite element constituting the ROI, to apply a predetermined load condition to a finite element model to which the elastic modulus is applied, to calculate a strain energy of each finite element based on the displacement of a finite element model to which the load condition is applied, and to determine a density value of each finite element based on the strain energy of each finite element.

According to another aspect, the image reconfigurer may be configured to segment the skeletal image into images including a plurality of finite elements, and the BMD of bone may indicate the BMD of bone corresponding to a finite element included in the ROI to be processed at the high resolution among the plurality of finite elements.

According to still another aspect, the image reconfigurer may be configured to reconstruct the high-resolution skeletal image by determining a new BMD of the ROI by performing the topology optimization and by iteratively performing an operation of converting the new BMD to an elastic modulus.

According to embodiments of the present invention, there is provided an apparatus for reconstructing a skeletal image, the apparatus including a memory to which at least one program is loaded, and at least one processor, wherein, according to a control of the program, the at least one processor is configured to process a process of determining an ROI to be processed at a high resolution with respect to a skeletal image captured from an inspection target, and a process of reconstructing a high-resolution skeletal image by performing an FEM and topology optimization on the ROI.

According to an aspect, the process of reconstructing the skeletal image may include a process of performing meshing on the skeletal image including the ROI, a process of converting a BMD of bone corresponding to the meshed ROI to an elastic modulus, a process of applying the elastic modulus to each finite element constituting the ROI, a process of applying a predetermined load condition to a finite element model to which the elastic modulus is applied, a process of calculating a strain energy of each finite element based on the displacement of a finite element model to which the load condition is applied, and a process of determining a density value of each finite element based on the strain energy of each finite element.

According to another aspect, as non-transitory computer-readable storage media including an instruction to control a computer system to provide a skeletal image, the instruction may control the system by a method including determining an ROI to be processed at a high resolution with respect to a skeletal image captured from an inspection target, and reconstructing a high-resolution skeletal image by performing an FEM and topology optimization on the ROI.

According to an aspect, the instruction may control the computer system by the method further including calculating a BMD of each finite element included in the ROI based on an objective function indicating a strain energy of the ROI and a predetermined constraint, and estimating presence or absence of lesion of the inspection target based on the calculated BMD and the skeletal image.

Effects

According to embodiments of the present invention, using a finite element method (FEM) and topology optimization, it is possible to reconstruct a high-resolution from which a bone micro-architecture is verifiable, without increasing an amount of radiation exposure and a scanning time.

Also, according to embodiments of the present invention, since an FEM and topology optimization are applied, it is possible to reconstruct a high-resolution image from which a bone micro-architecture is verifiable without purchasing a separate medical imaging device capable of performing high-resolution scanning.

Also, according to embodiments of the present invention, since a high-resolution image representing a bone mineral density (BMD) and a bone micro-architecture is also provided, it is possible to perform an early diagnosis for lesion associated with the BMD such as osteoporosis and to enhance the accuracy of diagnosis.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Figure 1:
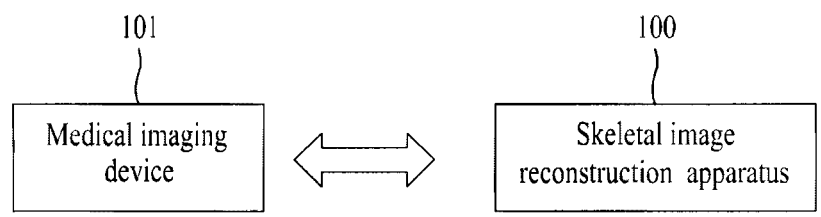
FIG. 1 is a diagram illustrating computed tomography (CT) according to an embodiment of the present invention.

Reference will now be made in detail to embodiments of the present invention, examples of which are illustrated in the accompanying drawings, wherein like reference numerals refer to like elements throughout. Embodiments are described below to explain the present invention by referring to the figures.

FIG. 1 is a diagram illustrating a configuration of a medical imaging device and a skeletal image reconstruction apparatus according to an embodiment of the present invention.

Referring to FIG. 1, the medical imaging device 101 may be a device to scan an inspection target to diagnose osteoporosis, to measure a bone mineral density (BMD), and to verify a bone micro-architecture.

Here, the medical imaging device 101 may include any type of medical device that converts strength of an image captured from the inspection target to modulus BMD. For example, the medical imaging device 101 may include any type of medical imaging device capable of converting strength of an image to a BMD, such as computed topography (CT), quantitative computed tomography (QCT), and magnetic resonance imaging (MRI). The inspection target refers to a predetermined body portion to be scanned for a BMD measurement, and may include, for example, a femoral region, a hip joint, a wrist, an ankle, a knee, and the lumbar.

As described above, the medical imaging device 101 may scan the inspection target, and may transmit scan information to the skeletal image reconstruction apparatus 100. For example, in the case of scanning the inspection target using the QCT, the QCT may detect X rays having transmitted the inspection target and may transfer the detected low-resolution data to the skeletal image reconstruction apparatus 100. The skeletal image reconstruction apparatus 100 may generate a low-resolution QCT image based on the transferred data.

The skeletal image reconstruction apparatus 100 may reconstruct a high-resolution skeletal image of 300 µm or less by performing a finite element method (FEM) and topology optimization based on a medical image. Here, the skeletal image reconstruction apparatus 100 may be connected to the medical imaging device 101 in a wired or wireless manner, and may be combined with the medical imaging device 101 in an add-on type. For example, the skeletal image reconstruction apparatus 100 may employ a computer system and a workstation.

Hereinafter, an operation of reconstructing a high-resolution skeletal image based on an FEM and topology optimization will be described with reference to FIGS. 2 and 3.

Figure 2:
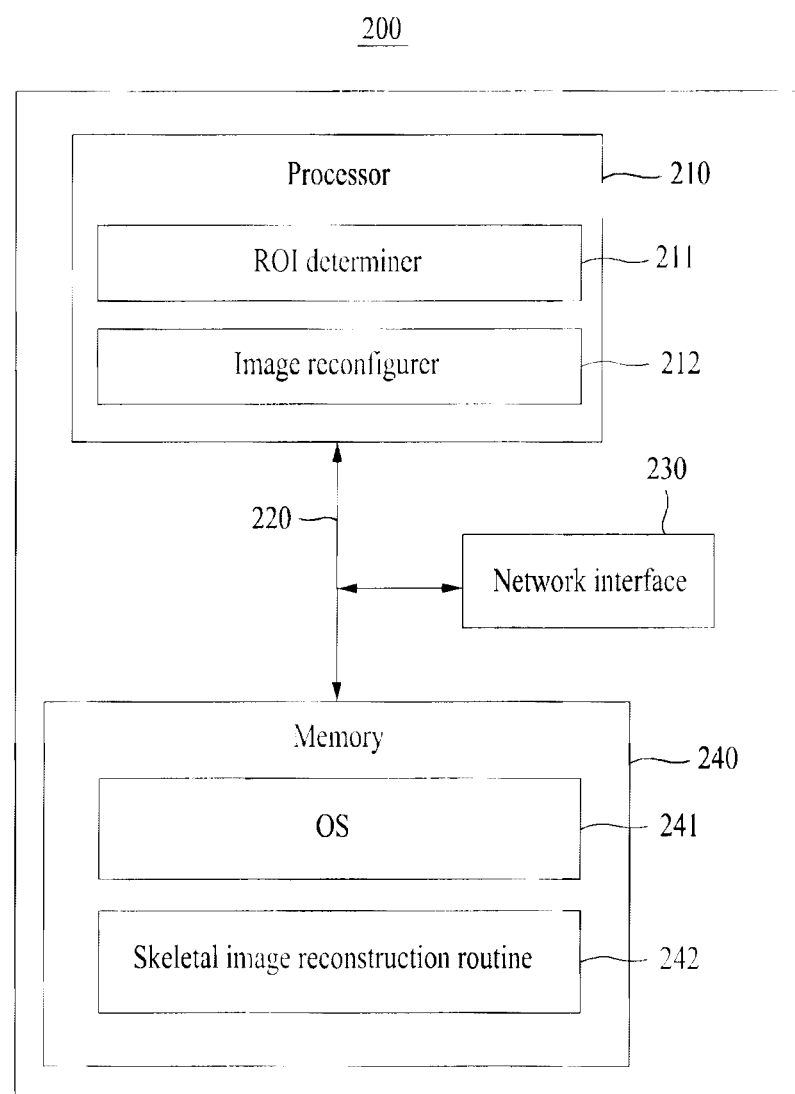
FIG. 2 is a block diagram illustrating a configuration of a skeletal image reconstruction apparatus according to an embodiment of the present invention.
Figure 3:
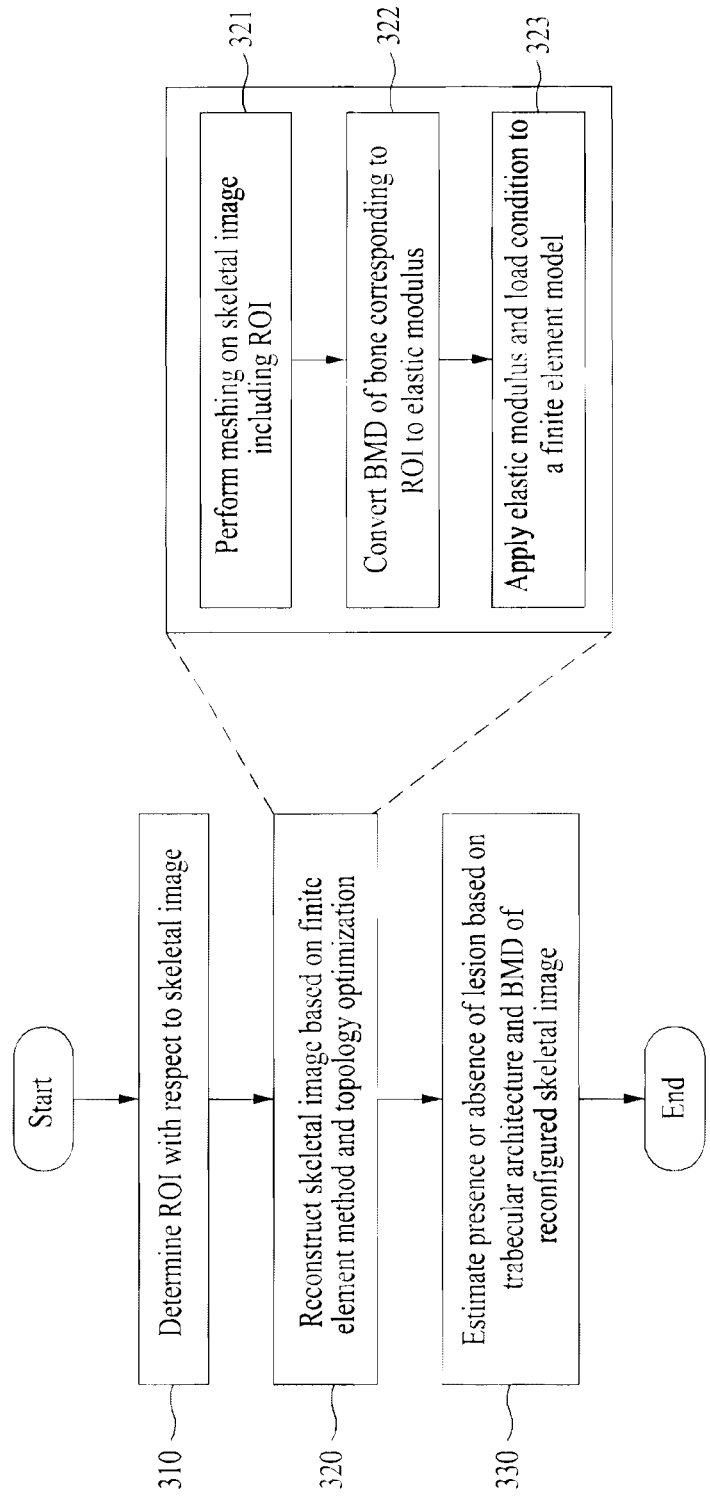
FIG. 3 is a flowchart illustrating a method of reconstructing a skeletal image according to an embodiment of the present invention.

FIG. 2 is a block diagram illustrating a configuration of a skeletal image reconstruction apparatus according to an embodiment of the present invention, and FIG. 3 is a flowchart illustrating a method of reconstructing a skeletal image according to an embodiment of the present invention.

Referring to FIG. 2, the skeletal image reconstruction apparatus 200 may include a processor 210, a bus 220, a network bus 230, and a memory 240. The memory 240 may include an operating system (OS) 241 and a skeletal image reconstruction routine 242. The processor 210 may include a region of interest (ROI) determiner 211 and an image reconfigurer 212. According to other embodiments, the skeletal image reconstruction apparatus 200 may include a further number of constituent elements compared to the number of constituent elements of FIG. 2. However, there is no need to clearly illustrate many constituent elements according to the related art. For example, the skeletal image reconstruction apparatus 200 may also include other constituent elements such as a display and a transceiver.

The memory 240, as non-transitory computer-readable recording media, may include a permanent mass storage device such as random access memory (RAM), read only memory (ROM), and a disk drive. Also, a program code for the OS 241 and the skeletal image reconstruction routine 242 may be stored in the memory 240. The software constituent elements may be loaded from non-transitory computer-readable media separate from the memory 240 using a drive mechanism (not shown). The non-transitory computer-readable media may include computer-readable media such as a floppy disk, a tape, a DVD/CD-ROM drive, and a memory card. According to other embodiments, the software constituent elements may be loaded to the memory 240 through the network interface 230, instead of using the non-transitory computer readable media.

The bus 220 may enable communication and data transmission between the constituent elements of the skeletal image reconstruction apparatus 200. The bus 220 may be configured using a high-speed serial bus, a parallel bus, a storage area network (SAN), and/or other appropriate communication technologies.

The network interface 230 may be a computer hardware constituent element to connect the skeletal image reconstruction apparatus 200 to a computer network. The network interface 230 may connect the skeletal image reconstruction apparatus 200 to the computer network through a wireless or wired connection.

The processor 210 may be configured to process an instruction of a computer program by performing a basic arithmetic and logic operation, and an input/output (I/O) operation of the skeletal image reconstruction apparatus 200. The instruction may be provided from the memory 240 or the network interface 230 to the processor 210 through the bus 220. The processor 210 may be configured to execute a program code for the ROI determiner 211 and the image reconfigurer 212. The program code may be stored in a storage device such as the memory 240.

The ROI determiner 211 and the image reconfigurer 212 may be configured to perform operations of FIG. 3.

In operation 310, the ROT determiner 211 may determine an ROI to be processed at a high resolution with respect to a skeletal image captured from an inspection target.

For example, the skeletal image may include a skeletal image of spine and a femur among a plurality of images segmented through image segmentation from a QCT image, a CT image, or an MIR image captured from the inspection target. The ROI determiner 211 may determine a predetermined portion to be processed at a high resolution among skeletal portions included in the skeletal image. For example, the ROI determiner 211 may determine, as a ROI, a region such as a femoral head corresponding to a head of the femur, a ward's triangle corresponding to an upper portion of the femur, and an intertrochanteric region corresponding to a lower portion of the femur.

Here, an image captured from the inspection target may represent a low-resolution image of 300 µm or more. For example, a resolution of the image captured from the inspection target may be about 600 µm.

In operation 320, the image reconfigurer 212 may reconstruct the skeletal image by performing an FEM and topology optimization on the ROI.

The image reconfigurer 212 may represent the ROI as a plurality of finite elements by performing meshing on the ROI. The image reconfigurer 212 may obtain a structural behavior value of each finite element by performing an FEM based on a BMD of bone corresponding to the meshed ROI, an elastic modulus, and a load condition. For example the image reconfigurer 212 may obtain a structural behavior value by converting the BMD to the elastic modulus, and by applying the converted elastic modulus and the load condition to a finite element model.

Figure 4:
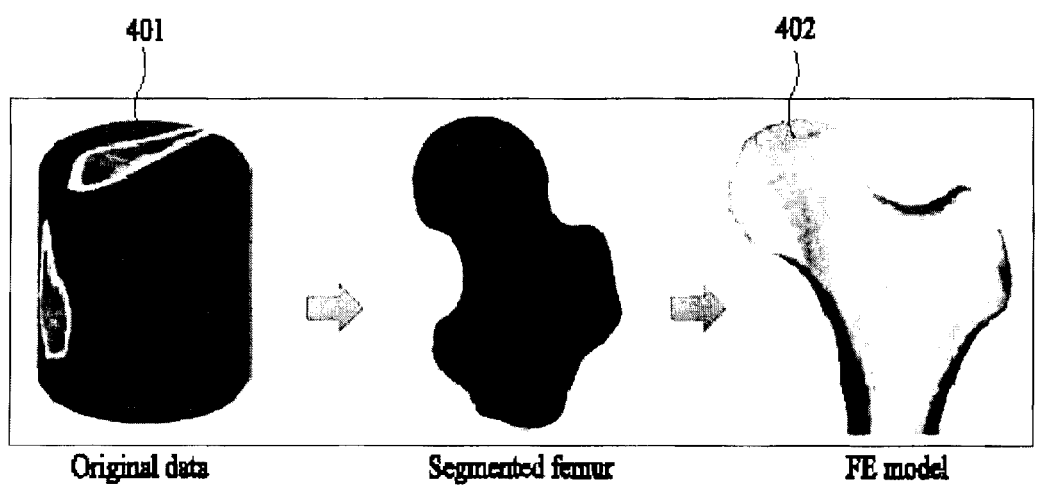
FIG. 4 illustrates an example of a finite element model generated based on a finite element method (FEM) according to an embodiment of the present invention.

Hereinafter, a process of applying an FEM to a skeletal image captured from an inspection target will be described. Referring to FIG. 4, a skeletal image 402 may be extracted by performing image segmentation on an image 401 captured from an inspection target, and a skeletal image reconstruction apparatus may apply an FEM to the skeletal image.

Finite Element Modeling (1) Perform meshing on an ROI to be processed at a high resolution with respect to a skeletal image.

(2) Allocate a physical property value of an individual finite element using a mathematical formulation between a BMD and an elastic modulus.

(3) Apply a load condition to an ROI.

(4) Obtain a structural behavior value of each finite element through an FEM.

Further describing the finite element modeling process, the image reconfigurer 212 may perform meshing with respect to the skeletal image including the ROI in operation 321. Here, the image reconfigurer 212 may perform meshing to segment the skeletal image into a plurality of images at a target resolution that is a desired high resolution. For example, when a resolution of the skeletal image is about 600 μm and a target resolution is 50 μm, the image reconfigurer 212 may perform meshing in order to segment the skeletal image into 12×12 images.

In operation 322, the image reconfigurer 212 may convert, to an elastic modulus, a BMD of bone corresponding to a finite element determined as the ROI among the meshed skeletal images. For example, the image reconfigurer 212 may convert the BMD to the elastic modulus based on a mathematical formulation in which a relationship between the BMD and the elastic modulus is predefined. Here, the image reconfigurer 212 may convert the BMD to the elastic modulus for each finite element included in the ROI.

In operation 323, the image reconfigurer 212 may apply the converted elastic modulus and the load condition to a finite element model. The load condition, as a set of load cases, may include one-legged stance abduction, and adduction. As the load condition is applied for a finite element model, a variation may occur in bone mass. In this case, the image reconfigurer 212 may perform topology optimization for finding a structure in which strain energy of bone corresponding to the ROI is minimized based on the variation.

For example, the image configurer 212 may extract a new BMD of the ROI in order to find a structure in which compliance is minimized. The image reconfigurer 212 may convert again the new BMD to an elastic modulus, and may recalculate strain energy since the converted elastic modulus is applied to the finite element. Here, when a difference value between the new BMD and a previous BMD used for strain energy calculation is less than or equal to a preset reference value, the image reconfigurer 212 may determine that topology optimization is completed and may terminate topology optimization. That is, the image reconfigurer 212 may determine that the strain energy calculated based on the previous BMD is the minimum strain energy.

Conversely, when the difference value is greater than the reference value, the image reconfigurer 212 may determine that the minimum strain energy is not found, and may continuously iterate an operation of calculating the strain energy by converting the new BMD to the elastic modulus and by applying the converted elastic modulus and the load condition to the finite element model. That is the image reconfigurer 212 may iteratively perform an FEM and topology optimization until the minimum strain energy is obtained.

As described above, the image reconfigurer 212 may reconstruct a high-resolution image by performing topology optimization on the ROI. For example, the image reconfigurer 212 may reconstruct 625 μm of a low-resolution ROI to 300 μm or less, for example, 78 μm, of a high-resolution image. Accordingly, since a bone micro-architecture, for example, a trabecular architecture, of the ROI may be provided at a high resolution, it is possible to perform an early diagnosis for lesion associated with a BMD such as osteoporosis and to enhance the accuracy of diagnosis. Further, since an FEM and topology optimization are applied using an existing medical imaging device, it is possible to reconstruct a high-resolution image without additionally purchasing a high-resolution imaging device.

Topology optimization may indicate a method of reconstruct a structure having a maximum rigidity by redistributing a density of an element with respect to a preset load condition with minimum mass. Accordingly the image reconfigurer 212 may reconstruct a bone micro-architecture capable of obtaining a maximum mechanical efficiency by reorienting the trabeculae with respect to the preset mechanical stimulus with the minimum bone mass. Here, the mechanical stimulus may represent a force applied to the femur and the like when a target is standing or running. That is the image reconfigurer 212 may reconstruct a high-resolution bone micro-architecture image by performing a bone reconstruction process through topology optimization based on low-resolution bone mass data.

Figure 5:
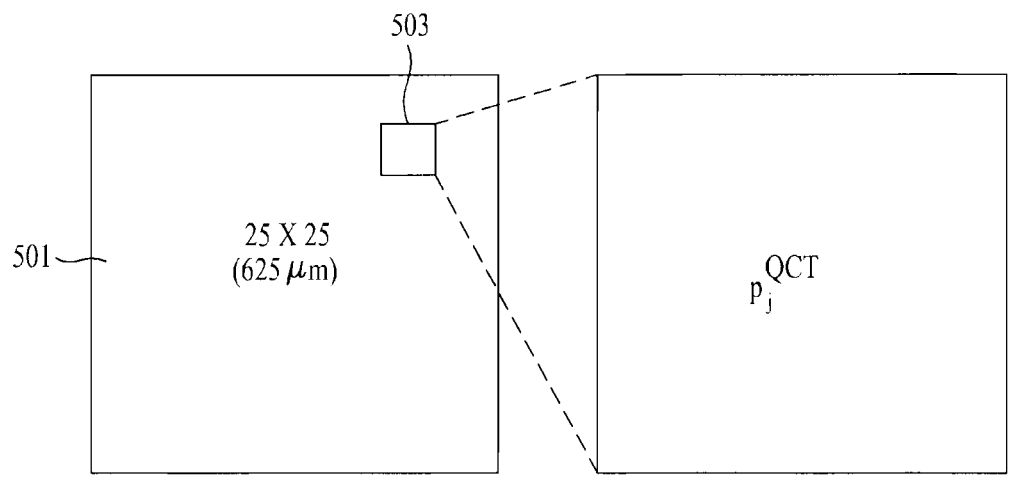
FIG. 5 illustrates a topology optimization process according to an embodiment of the present invention.
Figure 5:
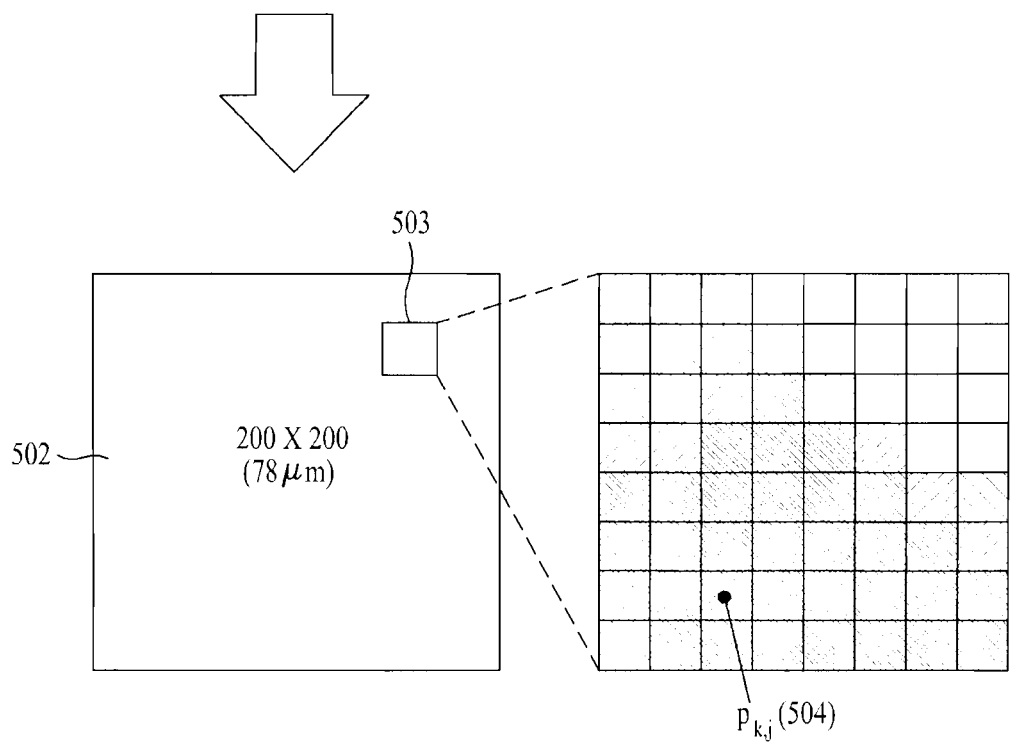

For example, the image reconfigurer 212 may perform topology optimization until the compliance is minimized. Hereinafter, a process of performing topology optimization will be described with reference to FIG. 5. Here, the compliance denotes an inverse number of rigidity. If the rigidity is high, the compliance may be low. If the rigidity is low, the compliance may be high. Referring to FIG. 5, a low-resolution image may include 625 $\rho_j^{QCT}$, and a high-resolution image may be reconfigured by segmenting individual $\rho_j^{QCT}$ to be plural. That is, the structural rigidity may be optimized with respect to the mechanical load while using the density distribution of the low-resolution image as is.

Topology Optimization (1) Setting a design variable

A BMD 504 of an individual finite element, for example, a pixel of a high-resolution image (2) Setting of an objective function Compliance minimization of an ROI 503

(3) Setting of constraints

A difference between a pixel value of a low-resolution image 501 and an average value of pixels constituting an image 502 processed at a high resolution (4) An optimal BMD in an individual finite element, for example, a pixel that satisfies an objective function and constraints is calculated through topology optimization. That is, a bone structure having the maximum rigidity through topology optimization is to be found according to Equation 1.

(5) A high-resolution skeletal image in an ROI is reconstructed.

According to Equation 1, a high-resolution skeletal image may be reconstructed through the aforementioned topology optimization process.

Minimize [Equation 1]

$$f(\rho_{k,j}) = \sum_{i=1}^{I} c_i \left( \frac{1}{2} u_i^T K u_i \right)$$

-continued

Subject to $$g(\rho_{k,j}) = \frac{1}{m}\sum_{j=1}^{m}\left(\frac{\sum_{k=1}^{n}\rho_{k,j}}{n} - \rho_l^{QCT}\right)^2 \le \varepsilon$$

$$0.01 \le \rho_{k,j} \le 1.0$$

where $\rho_{k,j}$ is a density of kth element in the jth division
$\rho_j$ is a density of jth division obtained from a device
$\varepsilon$ is a sufficiently small positive value
m is the total number of divisions
n is the total number of elements in the jth division
l is the total number of load cases In Equation 1, an objective function f($\rho$) denotes compliance, a density $\rho$ that is a design variable denotes a variable of compliance, and a constraint function g($\rho$) denotes an average difference value between pixels of a low-resolution image and a high-resolution image. The difference between the pixels may be within a predetermined tolerance (epsilon). That is, a bone microstructure may be generated by following the density distribution of the low-resolution image within the tolerance. $u_i$ denotes a displacement of each element when a force $F_1$ is applied, and K denotes a stiffness matrix.

As described above, according to Equation 1, the image reconfigurer 212 may calculate a BMD of each finite element included in the ROI based on the constraints and the objective function denoting the compliance of the ROI. That is, the image reconfigurer 212 may find a finite element corresponding to a density at which the rigidity for a preset mechanical force F becomes maximum through topology optimization according to Equation 1, and may reconstruct a high-resolution bone micro-architecture.

In operation 330, the image reconfigurer 212 may estimate presence or absence of lesion of the inspection target such as osteoporosis based on a BMD of each finite element included in the ROI and a reconstructed skeletal image corresponding to the ROI. For example, the image reconfigurer 212 may estimate presence or absence of lesion in a skeletal system of the inspection target based on a BMD and a trabecular architecture shown in the skeletal image. The image reconfigurer 212 may provide an estimation result to a medical team.

Although it is described that presence or absence of osteoporosis is estimated based on a calculated BMD and a trabecular architecture, it is only an example and thus, the image reconfigurer 212 may display the BMD and the trabecular architecture on a display (not shown) so that the medical team may make a diagnosis. In this example, the medical team may verify a location at which a disconnection has occurred based on the trabecular architecture, and may diagnosis osteoporosis based on the BMD.

Figure 6:
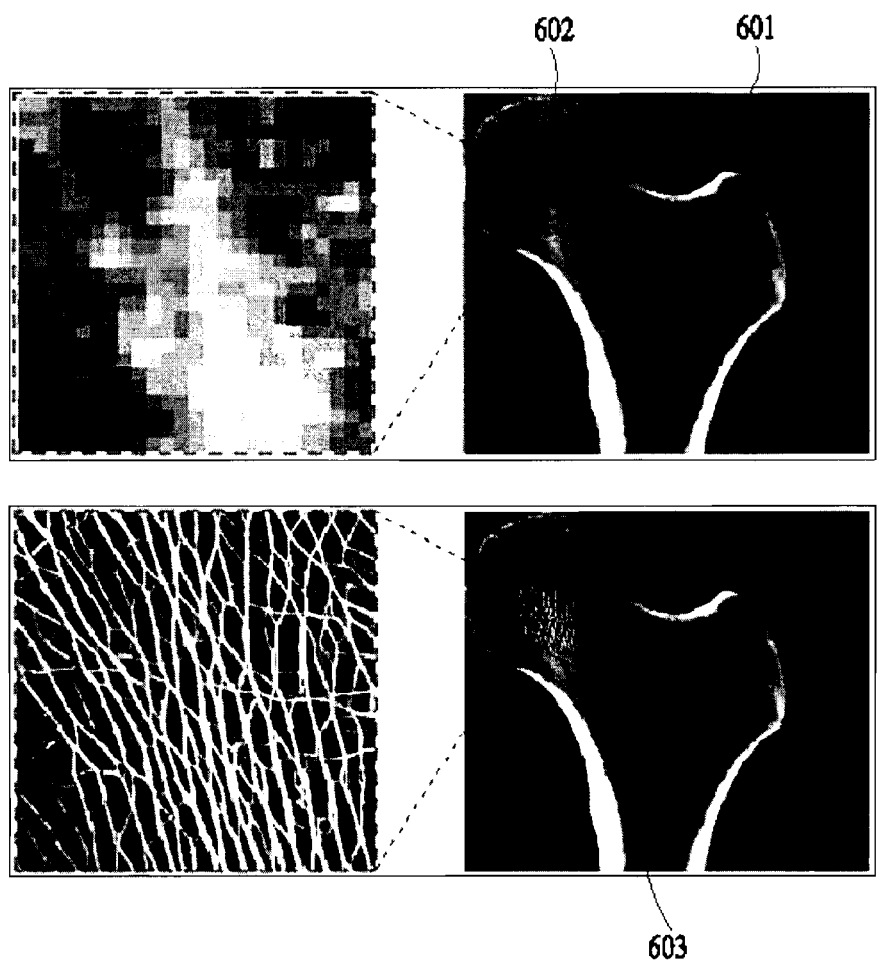
FIG. 6 illustrates a region of interest (ROI) processed at a high resolution according to an embodiment of the present invention.

FIG. 6 illustrates an ROI processed at a high-resolution according to an embodiment of the present invention.

Referring to FIG. 6, since a resolution of an original image 601 captured from a proximal femur using, for example, CT, QCT, and MRI is a 625 µm low resolution, a bone micro-architecture of an ROI 602 corresponding to a femoral head in the original image 601 shows that pixels are mostly broken and thus, do not clearly appear. Accordingly, the bone micro-architecture of the ROI 602 may not be readily utilized for osteoporosis diagnosis.

It can be verified that a resolution of a skeletal image 603 reconstructed by applying an FEM and topology optimization to the ROI 602 of the original image 601 is enhanced to be 78 µm. As described above, when a resolution of a reconstructed skeletal image is enhanced to be less than or equal to 300 µm, it is possible to clearly verify a bone micro-architecture of an ROI corresponding to a femur. Accordingly, it is possible to perform early diagnosis for osteoporosis based on a bone micro-structure and to increase the accuracy of diagnosis. In addition, a scanning time required to secure the same resolution is reduced, thereby saving medical expenses.

Figure 7:
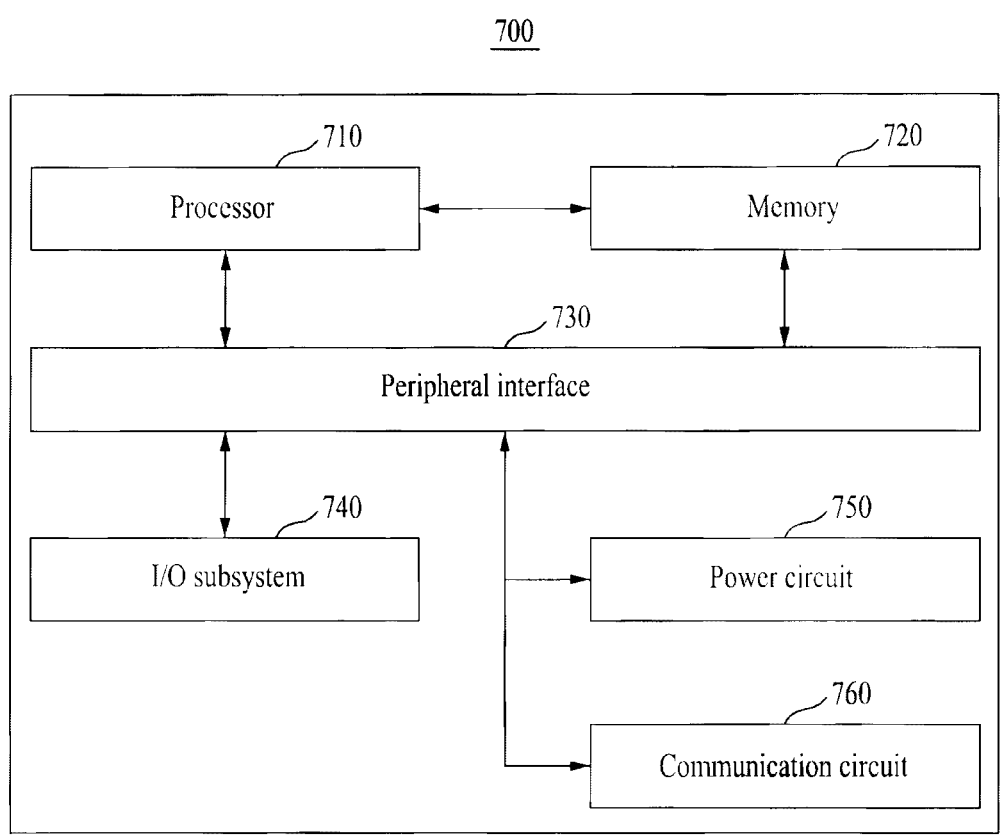
FIG. 7 is a block diagram illustrating an example of a configuration of a computer system according to an embodiment of the present invention.

FIG. 7 is a block diagram illustrating an example of a configuration of a computer system according to an embodiment of the present invention. The computer system 700 may include at least one processor 710, a memory 720, a peripheral interface 730, an input/output (I/O) subsystem 740, a power circuit 750, and a communication circuit 760. Here, the computer system 700 may correspond to a workstation.

The memory 720 may include for example a high speed random access memory (HSRAM), a magnetic disk, a static random access memory (SRAM), a dynamic RAM (DRAM), read only memory (ROM), a flash memory, and a non-volatile memory. The memory 720 may include a software module, an instruction set, or a variety of data required for an operation of the computer system 700. Here, an access from another component such as the processor 710 and the peripheral interface 730 to the memory 720 may be controlled by the processor 710.

The peripheral interface 730 may couple an input device and/or output device of the computer system 700 with the processor 710 and the memory 720. The processor 710 may perform a variety of functions for the computer system 700 and process data by executing the software module or the instruction set stored in the memory 720.

The I/O subsystem 740 may couple various I/O peripheral devices with the peripheral interface 730. For example the I/O subsystem 740 may include a controller for coupling the peripheral interface 730 and a peripheral device such as a monitor, a keyboard, a mouse, a printer, and a touch screen or a sensor depending on a necessity. The I/O peripheral devices may be coupled with the peripheral interface 730 without using the I/O subsystem 740.

The power circuit 750 may supply a power to all of or a portion of components of a terminal. For example, the power circuit 750 may include a power management system, at least one power source such as a battery and alternating circuit (AC), a charge system, a power failure detection circuit, a power converter or inverter, a power status indicator, or other components for creating, managing and distributing power.

The communication circuit 760 enables communication with another computer system using at least one external port. Alternatively, as described above, the communication circuit 760 may enable communication with another computer system by including a radio frequency (RF) circuit and thereby transmitting and receiving an RF signal known as an electromagnetic signal.

The embodiment of FIG. 7 is only an example of the computer system 700. The to computer system 700 may have a configuration or an arrangement for omitting a portion of the components illustrated in FIG. 7, further including components not illustrated in FIG. 7, or coupling two or more components. For example the computer system 700 may further include a display and the like, in addition to the components of FIG. 7. Components includable in the computer system 700 may be configured as hardware that includes an integrated circuit specified for at least one signal processing or application, software, or a combination of hardware and software.

The methods according to the embodiments of the present invention may be configured in a program instruction form executable through various computer systems and thereby recorded in non-transitory computer-readable media.

The units described herein may be implemented using hardware components, software components, or a combination thereof. For example, a processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums.

The above-described embodiments of the present invention may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as floptical disks; and hardware devices that are specially configured to store and perform program instructions, such as read-only memory (ROM), random access memory (RAM), flash memory, and the like. Examples of program instructions include both machine code such as produced by a compiler and files containing higher level code that may be executed by the computer using an interpreter. The described hardware devices may be configured to act as one or more software modules in order to perform the operations of the above-described embodiments of the present invention, or vice versa.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A method of reconstructing a skeletal image, the method comprising:
    determining a region of interest (ROI) to be processed at a high resolution with respect to a skeletal image captured from an inspection target; and
    reconstructing a high-resolution skeletal image by performing a finite element method (FEM) and topology optimization on the ROI, wherein the reconstruction of the skeletal image comprises:
    performing meshing on the skeletal image comprising the ROI;
    converting a bone mineral density (BMD) or BMD-related value of bone corresponding to the meshed ROI to an elastic modulus;
    applying the elastic modulus to each finite element constituting the ROI;
    applying a predetermined load condition to a finite element model to which the elastic modulus is applied;
    calculating a strain energy of each finite element based on the displacement of a finite element model to which the load condition is applied; and
    determining a density value of each finite element based on the strain energy of each finite element.

2. The method of claim 1, wherein the performing of the meshing comprises segmenting the skeletal image into images comprising a plurality of finite elements, and
    the BMD of bone indicates the BMD of bone corresponding to a finite element comprised in the ROI to be processed at the high resolution among the plurality of finite elements.

3. The method of claim 1, wherein the reconstruction of the skeletal image comprises reconstructing the high-resolution skeletal image by determining a new BMD of the ROI by performing the topology optimization, and by iteratively performing an operation of converting the new BMD to an elastic modulus.

4. The method of claim 1, further comprising:
    calculating a BMD of each finite element comprised in the ROI based on an objective function indicating a strain energy of the ROI and a predetermined constraint; and
    estimating presence or absence of lesion of the inspection target based on the calculated BMD and the skeletal image.

5. The method of claim 1, wherein the high-resolution skeletal image comprises a trabecular bone architecture corresponding to the ROI.

6. The method of claim 1, wherein the high-resolution skeletal image indicates an image having a resolution of 300 μm or less.

7. An apparatus for reconstructing a skeletal image, the apparatus comprising:
    a region of interest (ROI) determiner configured to determine an ROI to be processed at a high resolution with respect to a skeletal image captured from an inspection target; and
    an image reconfigurer configured to reconstruct a high-resolution skeletal image by performing a finite element method (FEM) and topology optimization on the ROI by:
    performing meshing on the skeletal image comprising the ROI, converting a bone mineral density (BMD) or BMD-related value of bone corresponding to the meshed ROI to an elastic modulus;

applying the elastic modulus to each finite element constituting the ROI;

applying a predetermined load condition to a finite element model to which the elastic modulus is applied;

calculating a strain energy of each finite element based on the displacement of a finite element model to which the load condition is applied; and determining a density value of each finite element based on the strain energy of each finite element.

8. The apparatus of claim 7, wherein the image reconfigurer is configured to segment the skeletal image into images comprising a plurality of finite elements, and the BMD of bone indicates the BMD of bone corresponding to a finite element comprised in the ROI to be processed at the high resolution among the plurality of finite elements.

9. The apparatus of claim 7, wherein the image reconfigurer is configured to reconstruct the high-resolution skeletal image by determining a new BMD of the ROI by performing the topology optimization and by iteratively performing an operation of converting the new BMD to an elastic modulus.

10. The apparatus of claim 7, wherein the high-resolution skeletal image comprises a trabecular bone architecture corresponding to the ROI.

11. The apparatus of claim 7, wherein the high-resolution skeletal image indicates an image having a resolution of 300 µm or less.

12. An apparatus for reconstructing a skeletal image, the apparatus comprising:

a memory to which at least one program is loaded; and at least one processor, wherein, according to a control of the program, the at least one processor is configured to process:

a process of determining a region of interest (ROI) to be processed at a high resolution with respect to a skeletal image captured from an inspection target; and a process of reconstructing a high-resolution skeletal image by performing a finite element method (FEM) and topology optimization on the ROI, the process of reconstructing the skeletal image comprising:

a process of performing meshing on the skeletal image comprising the ROI;

a process of converting a bone mineral density (BMD) of bone corresponding to the meshed ROI to an elastic modulus;

a process of applying the elastic modulus to each finite element constituting the ROI;

a process of applying a predetermined load condition to a finite element model to which the elastic modulus is applied;

a process of calculating a strain energy of each finite element based on the displacement of a finite element model to which the load condition is applied; and a process of determining a density value of each finite element based on the strain energy of each finite element.

13. Non-transitory computer-readable storage media comprising an instruction to control a computer system to provide a skeletal image, wherein the instruction controls the system by a method comprising:

determining a region of interest (ROI) to be processed at a high resolution with respect to a skeletal image captured from an inspection target;

reconstructing a high-resolution skeletal image by performing a finite element method (FEM) and topology optimization on the ROI;

calculating a bone mineral density (BMD) of each finite element comprised in the ROI based on an objective function indicating a strain energy of the ROI and a predetermined constraint; and estimating presence or absence of lesion of the inspection target based on the calculated BMD and the skeletal image.

14. The apparatus of claim 7, wherein the image reconfigurer is configured to:

calculate a BMD of each finite element comprised in the ROI based on an objective function indicating a strain energy of the ROI and a predetermined constraint; and estimate presence or absence of lesion of the inspection target based on the calculated BMD and the skeletal image.

15. The apparatus of claim 12, wherein the process for performing of the meshing comprises segmenting the skeletal image into images comprising a plurality of finite elements, and the BMD of bone indicates the BMD of bone corresponding to a finite element comprised in the ROI to be processed at the high resolution among the plurality of finite elements.

16. The apparatus of claim 12, wherein the process for reconstruction of the skeletal image comprises:

a process for reconstructing the high-resolution skeletal image by determining a new BMD of the ROI by performing the topology optimization and by iteratively performing an operation of converting the new BMD to an elastic modulus.

17. The apparatus of claim 12, wherein the process for reconstruction of the skeletal image further comprises:

a process for calculating a BMD of each finite element comprised in the ROI based on an objective function indicating a strain energy of the ROI and a predetermined constraint; and a process for estimating presence or absence of lesion of the inspection target based on the calculated BMD and the skeletal image.

18. The computer-readable storage media of claim 13, wherein the reconstruction of the skeletal image comprises:

performing meshing on the skeletal image comprising the ROI;

converting a bone mineral density (BMD) or BMD-related value of bone corresponding to the meshed ROI to an elastic modulus;

applying the elastic modulus to each finite element constituting the ROI;

applying a predetermined load condition to a finite element model to which the elastic modulus is applied;

calculating a strain energy of each finite element based on the displacement of a finite element model to which the load condition is applied; and determining a density value of each finite element based on the strain energy of each finite element.

19. The computer-readable storage media of claim 18, wherein the performing of the meshing comprises segmenting the skeletal image into images comprising a plurality of finite elements, and the BMD of bone indicates the BMD of bone corresponding to a finite element comprised in the ROI to be processed at the high resolution among the plurality of finite elements.

20. The computer-readable storage media of claim 13, wherein the reconstruction of the skeletal image comprises reconstructing the high-resolution skeletal image by determining a new BMD of the ROI by performing the topology optimization, and by iteratively performing an operation of converting the new BMD to an elastic modulus.

* * * * *